(12) United States Patent
Flower et al.

(10) Patent No.: US 6,522,919 B1
(45) Date of Patent: *Feb. 18, 2003

(54) IONTOPHORETIC DRUG DELIVERY DEVICE HAVING HIGH-EFFICIENCY DC-TO-DC ENERGY CONVERSION CIRCUIT

(75) Inventors: Ronald J. Flower, Vernon, NJ (US); James Michael Devine, Lower Burrell, PA (US)

(73) Assignee: Vyteris, Inc., Fair Lawn, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/718,135

(22) Filed: Nov. 21, 2000

Related U.S. Application Data

(63) Continuation of application No. 08/520,521, filed on Aug. 29, 1995, now Pat. No. 6,167,301.

(51) Int. Cl.⁷ ............................. A61N 1/30; A61N 1/08
(52) U.S. Cl. .......................................... 604/20; 607/62
(58) Field of Search ...................... 604/20, 21; 607/62, 607/63

(56) References Cited

U.S. PATENT DOCUMENTS 4,141,359 A    2/1979   Jocobsen et al.
5,047,007 A    9/1991   McNichols et al.
5,246,418 A    9/1993   Haynes et al.
5,254,081 A   10/1993   Maurer et al.
5,499,967 A    3/1996   Teillaud et al.
6,167,301 A *  12/2000  Flower et al. ................ 604/20

* cited by examiner

Primary Examiner—Michael J. Hayes
(74) Attorney, Agent, or Firm—Kirkpatrick & Lockhart LLP

(57) ABSTRACT

An iontophoresis system includes a transdermal patch for placement against the skin of a patient and a controller electrically connected to the patch. The patch includes an anode and cathode electrode, and holds an electrolyte and a medication. The controller includes a DC-DC converter circuit which generates an output voltage that is provided to the anode electrode. The controller also includes an adjustable current regulator circuit. The current regulator circuit is coupled to the cathode electrode and is adjustable to provide a desired current flow through the electrodes and the skin of the patient. The DC-DC converter circuit is responsive to the voltage drop across the electrodes and adjusts its output voltage in response to this voltage drop and changes in the impedance of the patient's skin.

1 Claim, 2 Drawing Sheets

IONTOPHORETIC DRUG DELIVERY DEVICE HAVING HIGH-EFFICIENCY DC-TO-DC ENERGY CONVERSION CIRCUIT

CROSS-REFERENCE TO RELATED APPLICATION

The present application is a continuation of U.S. patent application Ser. No. 08/520,521 filed Aug. 29, 1995, now issued as U.S. Pat. No. 6,167,301.

BACKGROUND OF THE INVENTION

1. Field of the Invention

The present invention generally relates to iontophoretic drug delivery devices, and more particularly relates to electronic circuits for use in iontophoretic drug delivery devices which deliver a controlled voltage or current to a patient receiving medication transdermally.

2. Description of the Prior Art

Iontophoresis may be defined as the electrically driven application of drugs or medications, in their ionic form, to the surface tissues of a patient. The application of electric current causes the migration of ions into the tissue, where such migration is proportional to the quantity of current applied through the iontophoretic system.

A basis iontophoretic device includes a controller and a drug delivery device, commonly called a transdermal patch. The controller may include a power source and a circuit to control the application of voltage or current from the power source to the patch. The patch generally includes two or more electrodes, the ionic medication and an electrolyte. When the patch is placed against the skin of the patient and a voltage is impressed across the electrodes, a circuit through the patient's skin is created and current flows through the skin of the patient, driving the ionic medication into the skin and tissue to be absorbed by the patient's body.

In some applications, it may be desirable to increase the voltage provided to the patch electrodes from the power source. This is especially true when the iontophoretic device is battery powered, and it may be necessary to increase a relatively low battery voltage to a higher, but safe, electrode voltage to more effectively drive the ionic medication into the skin and tissue of the patient. In such applications, a boost circuit or step-up DC-DC converter may be suitable for use, such as shown in FIG. 4 of U.S. Pat. No. 5,306,235.

OBJECTS AND SUMMARY OF THE INVENTION.

It is an object of the present invention to provide an improved circuit design for an iontophoretic drug delivery device.

It is another object of the present invention to provide a high efficiency DC-DC converter circuit for use in an iontophoresis system.

It is a further object of the present invention to provide a self-regulating DC-DC converter circuit for an iontophoresis system which adjusts to changes in the impedance of the tissue of a patient undergoing iontophoresis.

It is yet a further object of the present invention to provide a DC-DC converter circuit which adjusts its output voltage in response to a desired drug delivery current or to variations in the impedance of a patient undergoing iontophoresis.

It is yet another object of the present invention to provide a DC-DC converter circuit which is at least partially failsafe to prevent undesired current flow to a patient undergoing iontophoresis.

In accordance with one form of the present invention, an iontophoresis system includes an iontophoretic drug delivery device, commonly called a patch, for placement against the skin of a patient, and a controller electrically connected to the patch and having circuitry for controlling current and voltage provided to the patch. More specifically, the patch includes at least a first electrode, which may act as an anode, and at least a second electrode, which may act as a cathode. The patch also includes containers or other structure for holding an electrolyte and a medication. The electrolyte and medication are situated on the patch such that they are in electrical communication with one or the other of the first and second electrodes.

The controller of the iontophoresis system includes a DC-DC converter circuit. The DC-DC converter circuit generates an output voltage which is provided to at least one of the first and second electrodes.

The controller also includes an adjustable current regulator circuit. The current regulator circuit is coupled to the other electrode and is adjustable to provide a desired current flow through the first and second electrodes and the skin of the patient when the patch, is placed on the patient's skin.

The DC-DC converter circuit is responsive to the voltage drop across the first and second electrodes. The circuit adjusts its output voltage in response to this voltage drop to provide just the voltage needed across the electrodes and adjustable current regulator for safe and effective drug delivery to the patient without the wasteful consumption of power. The controller circuitry, which includes both the DC-DC converter circuit and the adjustable current regulator circuit, is also particularly responsive to any sudden changes in current or voltage provided to the patch, such as if the patient's skin impedance suddenly changed or the current regulator circuit is adjusted to provide a different drug delivery current to the patient during the iontophoretic process.

These and other objects, features and advantages of the present invention will become apparent from the following detailed description of illustrative embodiments thereof, which is to be read in connection with the accompanying drawings.

DETAILED DESCRIPTION OF THE PREFERRED EMBODIMENTS

Figure 1:
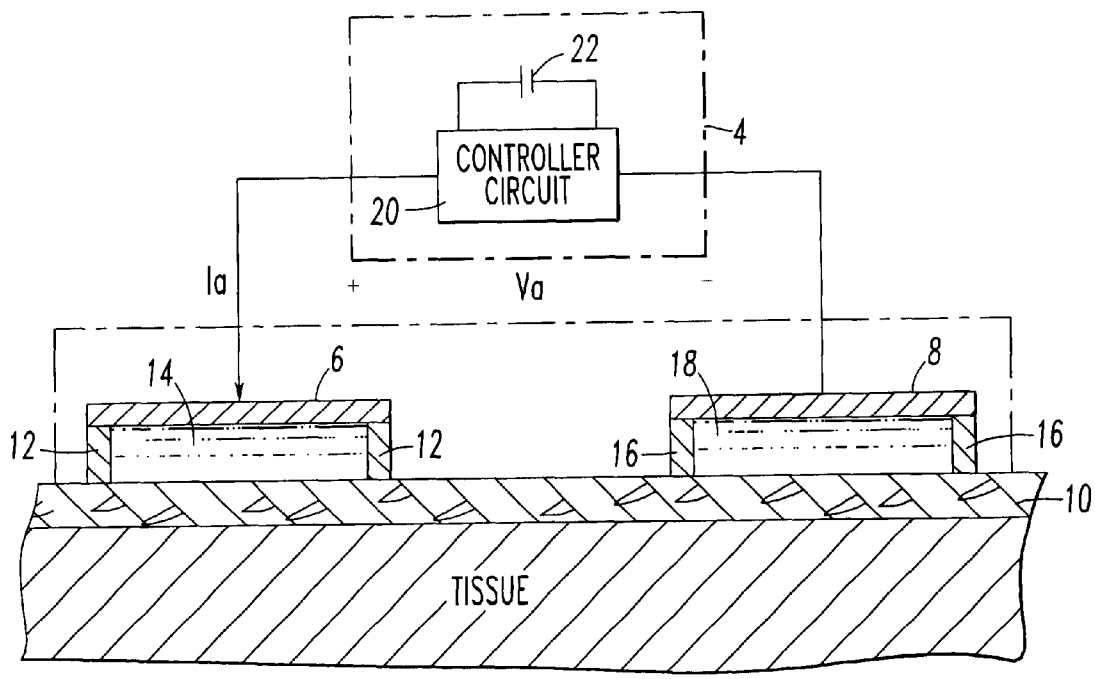
FIG. 1 is a block diagram of an iontophoresis system formed in accordance with the present invention, with portions thereof shown in cross-section.

Referring initially to FIG. 1 of the drawings, it will be seen that an iontophoresis system for delivering medication to a patient transdermally, that is, through the skin of the patient, basically includes a transdermal drug delivery device, commonly referred to as a patch 2, for placement against the skin of a patient, and a controller 4 which is electrically coupled to the patch One form of a transdermal drug delivery device (i.e., the patch 2) is illustrated by FIG. 1. The transdermal patch basically includes a first electrode 6, which may act as an anode, and a second electrode 8, which may act as a cathode.

The patch is placeable against the skin 10 of a patient so that the anode electrode 6 and cathode electrode 8 are in electrical communication with the patient's skin.

Adjacent to the anode (i.e., the first electrode 6) is a container 12 or other suitable structure defining a well for holding a medication 14 in place between the anode 6 and the skin 10 of the patient. Similarly, adjacent to the cathode (i.e., the second electrode 8) is a container 16 or other suitable structure forming a well for holding an electrolyte 18 in place between the cathode 8 and the skin 10 of the patient.

When a voltage Va is impressed across the first and second electrodes 6,8, current Ia will flow through the skin 10 of the patient, driving the medication 14, which may be ionic, into the skin and tissue to be absorbed by the patient's body. To simplify the explanation, only two electrodes are shown in FIG. 1. However, it should be understood that the anode and cathode may be segmented, or multiple electrodes may be provided, as is well known in the art.

Referring again to FIG. 1 of the drawings, the controller 4 of the iontophoresis system includes a current and voltage delivery circuit 20 which controls the current passing through each of the electrodes 6,8 and the voltage across the electrodes. The controller may also include a power source 22, such as a battery, which is connected to the current and voltage delivery circuit 20. The controller circuit 20 is connected to the transdermal patch 2 to provide a controlled current and voltage to the electrodes and thus the skin of the patient. As will become evident, the controller circuit 20 is advantageously designed with the capability of providing an adjustable but regulated drug delivery current and just the right voltage across the electrodes for proper drug delivery, and with the ability to react to sudden changes in voltage or current requirements due, for example, to changes in the patient's skin impedance or changes in the impedance of the transdermal patch.

Figure 2:
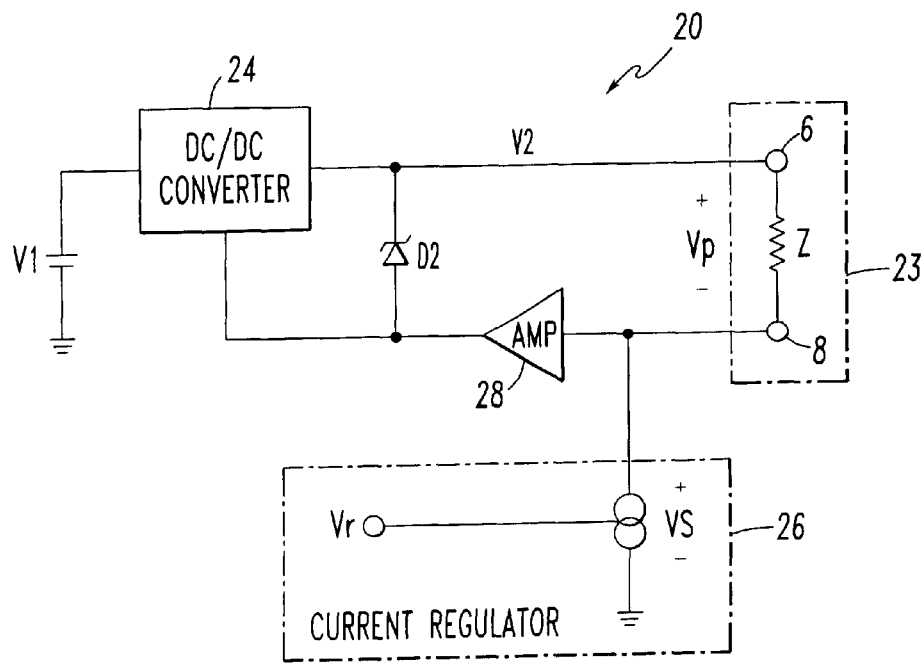
FIG. 2 is a block diagram of a circuit of the iontophoresis system formed in accordance with the present invention.

FIG. 2 illustrates in block diagram form one form of the controller circuit used in the present invention. The power source or battery 22 is designated as voltage V1. The load impedance Z represents the impedance of the patch/patient circuit 23. More specifically, impedance Z includes the impedance of the transdermal patch 2, such as the impedance of the electrodes 6,8, the medication 14 and electrolyte 18 and the impedance of the connection between the transdermal patch and the patient, as well as the impedance of the patient's skin 10.

As shown in FIG. 2, the controller circuit 20 includes a DC-DC converter circuit 24. The DC-DC converter circuit is connected to the power source (represented by voltage V1) and generates an output voltage V2 which is provided between ground and at least one of the electrodes, such as the anode 6, of the transdermal patch. The DC-DC converter 24 may be a step-up converter which effectively increases the voltage V1 of the power source and generates an output voltage V2. Such a step-up converter would be useful in a portable iontophoresis system which is battery powered and which is worn by the patient during an iontophoretic session.

Alternatively, it is envisioned that the DC-DC converter 24 may provide an output voltage V2 which is equal to the power source voltage V1, in order to isolate the patient directly from the power source, or may even be a step-down converter, providing an output voltage V2 which is less than the voltage V1 of the power source. In any event, it is preferred if the DC-DC converter 24 is adjustable so that it may vary the output voltage V2 in response to a control signal (such as a fed back voltage level) provided to it. A preferred form of a DC-DC converter will be described in relation to FIG. 3.

As shown in FIG. 2, the controller circuit 20 also includes an adjustable current regulator circuit 26. The adjustable current regulator circuit 26 is coupled to the other electrode, such as the cathode 8, of the transdermal patch 2 and is adjustable to provide a desired current flow through the first and second electrodes and the skin 10 of the patient undergoing iontophoresis. The current regulator circuit 26 may be a series pass regulator, for example, and may be controlled by a voltage Vr on an input of the circuit. By adjusting voltage Vr, the current regulator circuit will source or sink a desired drug delivery current flowing through the patch electrodes 6,8 and skin 10 of the patient.

The voltage on the second electrode, or cathode 8, may be fed back to the DC-DC converter circuit 24 through a buffer amplifier 28 or the like so that the DC-DC converter circuit will be responsive to the voltage drop across the current regulator 26 and, indirectly, across the first and second electrodes 6,8. The DC-DC converter circuit 24 is designed to provide just the necessary voltage across the electrodes and current regulator for proper drug delivery and in order to minimize power consumption, and it does this in response to the voltage provided to it from the cathode 8.

The controller circuit 20 of the present invention shown in FIG. 2 operates in the following manner. A voltage Vr is selected and applied to the current regulator circuit 26 which will cause a corresponding desired drug delivery current to flow through the electrodes 6,8 of the transdermal patch 2 and through the patient's skin 10 when the patch is placed on the patient. The patient and patch together will have a particular impedance Z, which may vary as will be further explained.

For example, if the impedance of the patch and patient together is 15,000 ohms, and the desired drug delivery current flowing through the patch and patient is set for 2 milliamperes, then by Ohm's law, there will be a voltage drop Vp across the patch/patient circuit 23 of 30 volts. These would be, as an example, the expected impedance and desired drug delivery current flow during the iontophoresis session for a particular medication being applied transdermally. Under these circumstances, the DC-DC converter, 24 will be initially configured to step-up the battery voltage V1 to a safe but more useful output voltage V2 which is applied to one of the electrodes 6,8 of the patch to provide the necessary voltage across the patch/patient circuit 23 and the current regulator 26 and thus ensure that the necessary at least 30 volts is available across the patch and that the desired current flow of 2 milliamperes is not limited to a lower value.

The DC-DC converter 24 is designed so that there will be only a minimal voltage drop Vs across the adjustable current regulator circuit. In other words, the output voltage V2 of the DC-DC converter 24 is equal to the sum of voltage Vp and voltage Vs, since the patch/patient circuit 23 is in series with the current. regulator circuit 26 and voltage V2 is provided across the series connection of the current regulator circuit 26 and patch/patient circuit 23. The voltage at the cathode 8 of the transdermal patch 2 is applied through the buffer amplifier 28 to the voltage control input of the DC-DC converter 24 so that the iontophoresis system is stable and providing a safe, regulated voltage at the desired drug delivery current with minimal wasteful voltage drop across the current regulator circuit 26.

However, it is known that the impedance of a patient's skin can range from over 100,000 ohms to nearly 1,000 ohms, depending on the duration that the iontophoretic current is applied, the magnitude of the current which is being delivered, the location of the system on the patient's body, and other factors. In a system where the desired current level, which is determined in part by the drug administered to the is patient, is 2 milliamperes, a voltage potential of 100 volts would result if the skin impedance is 50,000 ohms. Such a voltage would cause undesirable sensations to the user and may result in skin irritation or burns. The system of the present invention is self-regulating to ensure that this will not occur and at the same time providing the minimum voltage necessary for drug delivery.

If, for example, the impedance of the patient (and patch) were not the expected 15,000 ohms in the example given above but rather was 50,000 ohms, which is more likely to happen at the start of iontophoresis, then the voltage drop Vp across the patch/patient circuit 23 would be 100 volts at the desired current of 2 milliamperes. To prevent this, the DC-DC converter 24 is preferably self-limiting to provide a pre-selected maximum voltage, such as 30 volts, to the patch. By Ohm's law, the current flowing through the patient's skin would then be reduced to 0.6 milliamperes, as opposed to the desired drug delivery current of 2 milliamperes selected to be applied by the adjustable current regulator circuit at the average expected skin impedance (i.e., 15,000 ohms).

Alternatively, if a DC-DC converter 24 is selected which is not self-limiting, an external zener diode D2 may be used and situated effectively in parallel with the patch/patient circuit 23. As shown in FIG. 2, the zener diode D2 is connected with its cathode coupled to the output of the DC-DC converter 24 and the first electrode 6, and with its anode coupled between the output of the buffer amplifier 28 and the voltage control input of the DC-DC converter 24. A 30 volt (or other value) zener diode D1 may be selected to ensure that the voltage drop Vp across the patch/patient circuit 23 does not exceed a predetermined safe value. Thus, the controller circuit 20 provides a regulated voltage to the transdermal patch 2, which voltage is limited to prevent undesirable irritation or burns to the patient.

The controller circuit 20 will also self-regulate to apply to the patch 2 only the voltage necessary at the desired iontophoretic current should the impedance of the patient (or patch) suddenly decrease. Returning to the example given above, should the impedance of the patch/patient circuit 23 suddenly decrease from 15,000 ohms to 10,000 ohms, the voltage drop Vp across the patch would now only be 20 volts. The controller circuit is designed to react to sudden changes such that the 10 volt difference between the output voltage of the DC-DC converter 24 and the 20 volt drop across the patch will immediately be dropped across the adjustable current regulator circuit 26. Since, steady-state, this is wasteful and not energy efficient, the DC-DC converter 24 will sense the voltage at the cathode 8 of the transdermal patch and readjust the output voltage V2 of the converter to a lower value, for example, to effect a voltage drop Vp of 20 volts across the patch electrodes 6,8, i.e., the lowest voltage necessary to conduct iontophoresis with the desired drug delivery current flow, and to minimize the voltage drop Vs across the current regulator circuit 26 in order to reduce power consumption and heat generation and to prolong the life of the battery supplying voltage V1. Thus, the controller circuit of the present invention not only reacts to sudden changes in the impedance of the patient (and patch), but also is self-regulating to prevent skin irritation and burns and to reduce power consumption.

Figure 3:
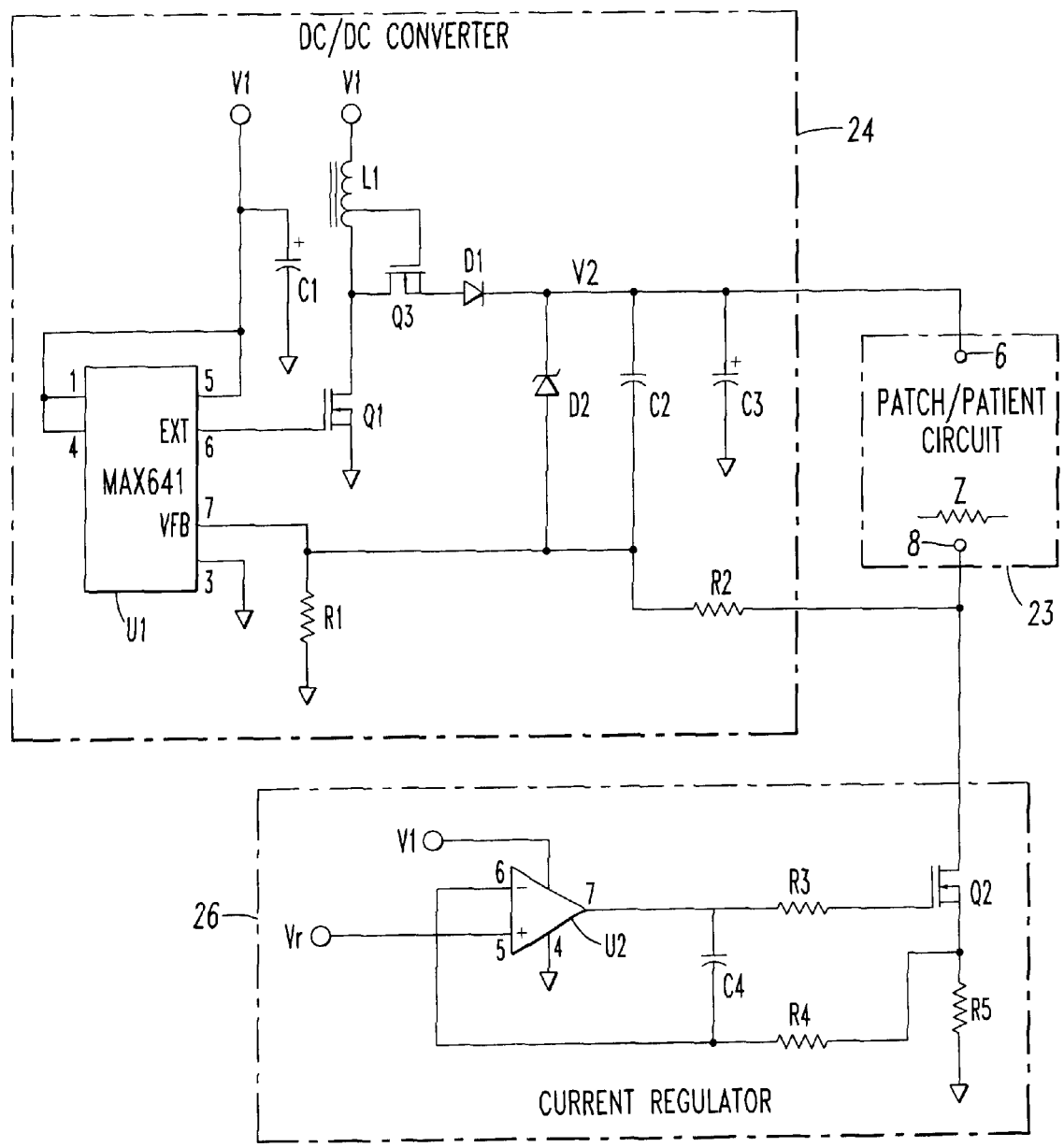
FIG. 3 is a detailed schematic diagram of the circuit shown in FIG. 2 of the iontophoresis system formed in accordance with the present invention.

FIG. 3 is a detailed schematic of a preferred form of a controller circuit 20 constructed in accordance with the present invention. The adjustable current regulator circuit 26 is shown as a series pass regulator comprising MOSFET transistor Q2, resistors R3-R5, capacitor C4 and operational amplifier U2.

More specifically, voltage Vr, for adjusting the controlled current flowing through the patch, is provided to the non-inverting input of operational amplifier U2. The output of amplifier U2 is provided through resistor R3 to the gate of transistor Q2. The drain of transistor Q2 is connected to resistor R5, whose other end is grounded, and is also connected, through resistor R4, to the inverting input of amplifier U2. Capacitor C4 may be provided between the output and inverting input of amplifier U2 to eliminate oscillations.

The current regulator circuit 26 operates as any conventional series pass regulator as is well known in the art. Amplifier U2 biases transistor Q2 on to control the current flowing through transistor Q2 and resistor R5 to that which is required to make the voltage drop across resistor R5 and provided to the inverting input of amplifier U2 equal to the voltage Vr applied to the control input of the current regulator circuit, i.e., the non-inverting input of amplifier U2. Thus, the voltage Vr applied to the circuit 26 will control the current flowing through transistor Q2. That current is the desired drug delivery current which will flow through the electrodes 6,8 of the transdermal patch 2 and through the patient's skin 10. As is well known, the current regulator circuit 26 shown in FIG. 3 is self-regulating and will maintain a constant current proportional to the voltage Vr applied to the circuit. As can be seen the source of transistor Q2 is connected to the cathode 8 of the transdermal patch 2.

The preferred DC-DC converter circuit 24 includes a step-up switching regulator integrated circuit U1, such as Part No. MAX 641 manufactured by Maxim Integrated Products of Sunnyvale, Calif. It is envisioned, of course, that other integrated circuits may be suitable for use, or a comparable DC-DC converter may be built using discrete components.

The step-up DC+DC converter 24 uses an external inductor L1 to store energy. An oscillator internal to the MAX641 integrated circuit U1 drives the gate of a MOSFET transistor Q1 from the EXT output of the integrated circuit, which switches the MOSFET transistor Q1 on and off. The drain of the transistor Q1 is coupled to one end of the inductor L1, the other end being provided with the battery voltage V1. The source of transistor Q1 is connected to ground. When the transistor Q1 is turned on, current flows through the inductor L1. The current increases linearly, storing energy in the inductor L1. When the EXT output switches transistor Q1 off, the inductor's magnetic field collapses, and the voltage across the inductor reverses polarity.

A diode D1, having its anode connected to the transistor side of the inductor L1 and its cathode connected to the anode 6 of the transdermal patch, is forward biased when the voltage at the diode's anode rises to a predetermined level, delivering power to the transdermal patch. A filter capacitor C3, coupled between the cathode of diode D1 and ground, filters the output voltage ripple.

If desired, the DC-DC converter circuit 24 may include an additional MOSFET transistor Q3 connected in series with diode D1 and biased on and off by connecting its gate to a tap of inductor L1. Transistor Q3 is provided to decrease leakage current through diode D1.

Not only does transistor Q3 reduce leakage current, but it also makes the DC-DC converter circuit of the present invention at least partially failsafe to prevent continued current flow to the patch should the step-up switching regulator integrated circuit U1 fail.

More specifically, the MAX641 integrated circuit U1 includes an internal oscillator which drives transistor Q1 on and off, as mentioned previously. If the oscillator output signal fails in the high state, transistor Q1 will saturate so that the source of transistor Q3 will be substantially at ground potential (i.e., the voltage drop across saturated transistor Q1). Transistor Q3, as well as diode D1, will be non-conducting, and no current will flow from the battery (providing voltage V1) to the patch.

However, if the oscillator internal to integrated circuit U1 failed such that the signal provided to the gate of transistor Q1 is in the low state, transistor Q1 will be cut off. Without transistor Q3, current could flow from the battery through inductor L1 and diode D1 (which is in a conducting state), and to the transdermal patch electrodes 6, 8 and patient.

Transistor Q3, however, because it is driven by the signal from the tap of inductor L1, turns on only during the collapse of the field generated by the inductor, i.e., only during a condition of flyback in the inductor. At all other times, including during storage of energy in inductor L1, transistor Q3 is non-conducting. Accordingly, should the step-up regulator integrated circuit U1 fail such that it biases transistor Q1 off, transistor Q3 will be turned off, and it will not allow current to flow from the battery through inductor L1 to the patch and patient.

When the output voltage V2 from the DC-DC converter 24 provided to the transdermal patch 2 reaches the desired level (for example, 30 volts), a comparator internal to the MAX641 integrated circuit U1 inhibits the signal on the EXT output, which turns off transistor Q1 to prevent further energy from being stored in the inductor L1 until the patch/patient circuit 23 discharges the output filter capacitor C3 to less than the desired output voltage level.

The MAX641 integrated circuit U1 provides an adjustable output voltage V2 which is controlled by forming a voltage divider using series interconnected resistors R1 and R2. Resistor R1 has one end connected to ground and another end connected to resistor R2, whose other end is connected to the cathode 8 of the transdermal patch 2 and the series current regulator 26. The VFB input of the MAX641 integrated circuit U1 is connected to the connection point between resistors R1 and R2. In this way, the voltage on the cathode 8 of the transdermal patch will be monitored and used to adjust the output voltage V2 of the DC-DC converter 24 provided to the patch and across the current regulator circuit 26. An optional 100 picofarad capacitor C2 may be connected between the cathode of diode D1 and the VFB input of the MAX641 integrated circuit U1 to prevent oscillations.

A zener diode D2 is also provided to prevent an overvoltage condition. Diode D2 has its cathode connected to the cathode of diode D1, and its anode connected to the VFB input of the MAX641 integrated circuit. The diode D2 will conduct in its breakdown region when the voltage drop Vp across the patch/patient circuit 23 exceeds a predetermined voltage. When zener diode D2 conducts, the VFB input of integrated circuit U1 will rise in voltage, turning off transistor Q1 and preventing further energy from being stored in inductor L1 until the output voltage V2 provided to the patch/patient circuit 23 falls below the breakdown voltage of diode D2. In effect, diode D2 will prevent the voltage drop Vp across the patch/patient circuit 23 from exceeding more than a predetermined, safe voltage. Such a situation could occur if the impedance of the patch/patient circuit exceeded a predetermined value.

During iontophoresis, should the impedance of the patch/patient circuit 23 suddenly decrease below a predetermined value, then the excess voltage not dropped across the patch/patient circuit is dropped across transistor Q2 of the current regulator circuit 26. Thus, the controller circuit 20 has the capability of reacting to sudden impedance changes in the patch/patient circuit 23, such as when the patch is readjusted on the patient or the patient's skin impedance changes suddenly.

The power dissipation caused by the voltage drop across transistor Q2 is wasteful and inefficient and, accordingly, the DC-DC converter 24 readjusts itself to lower the voltage. V2 provided to the patch/patient circuit 23 to only that which is necessary for iontophoresis at the desired delivery current, thereby reducing the voltage drop across transistor Q2. The circuit does this by monitoring the voltage on the cathode 8 of the transdermal patch 2 and providing that voltage, albeit attenuated, to the VFB input of integrated circuit U1 through the resistor network formed by resistors R1 and R2. The energization of inductor L1 is controlled so that a lower voltage will now be generated by the DC-DC converter circuit 24 and provided to the electrodes 6,8 of the patch.

A parts list for the circuit shown in FIG. 4 is provided in Table I below. It is envisioned that components comparable to those listed below, connected differently to that shown in FIG. 4, may be suitable to practice the invention. The battery voltage V1 may be any voltage, such as about 2 volts to about 10 volts, or more preferably, about 4 volts to about 6 volts.

TABLE I

| PART | REFERENCE DESIGNATION |
| --- | --- |
| inductor 500 µH | L1 |
| diode 1N914B | D1 |
| diode 1N4713C 30 V | D2 |
| transistor VN2222LL | Q1, Q2, Q3 |
| step-up switching regulator MAX641 | U1 |
| operational amplifier MAX478 | U2 |
| capacitor 1 µF, 10 V | C1 |
| capacitor 100 pF | C2 |
| capacitor 1 µF, 35 V | C3 |
| capacitor 470 pF | C4 |
| resistor 261 kΩ | R1 |
| resistor 140 kΩ | R2 |
| resistor 1 kΩ | R3, R4 |
| resistor 500 Ω | R5 |

As can be seen from the above description, the iontophoresis system of the present invention, with its self-regulating DC-DC converter circuit 24, is highly efficient in providing the necessary power for transdermal drug delivery. The controller circuit 20 is responsive to changes in the impedance of the patient's skin and patch and adjusts the voltage and current provided to the patch as necessary, not only to prevent excessive voltage which can cause irritation or burns, but also to minimize the energy required to conduct iontophoresis effectively.

Although illustrative embodiments of the present invention have been described herein with reference to accompanying drawings, it is to be understood that the invention is not limited to those precise embodiments, and that various other changes and modifications may be effected therein by one skilled in the art without departing from the scope or spirit of the invention.

What is claimed is:

1. An iontophoresis system control circuit for use with an iontophoretic drug delivery device, the iontophoretic drug delivery device being placeable against the skin of a patient and having at least first and second electrodes, the control circuit comprising:

a series pass regulator circuit, the series pass regulator circuit being responsive to a control voltage and controlling a desired drug delivery current in response thereto, the desired drug delivery current being flowable through the at least first and second electrodes and the skin of the patient, the series pass regulator circuit having a voltage Vs thereacross, the series pass regulator circuit being electrically coupled to the at least second electrode of the iontophoretic drug delivery device;

a step-up DC-DC converter circuit, the step-up DC-DC converter circuit being electrically coupled to the at least first electrode and generating an output voltage V2 which is provided thereto, the impedance of at least one of the iontophoretic drug delivery device and the patient's skin and the desired drug delivery current flowing therethrough resulting in a voltage drop Vp across the at least first and second electrodes, wherein the voltage V2 is equal to the sum of the voltage Vp and the voltage Vs, the DC-DC converter circuit being responsive to the voltage Vp across the at least first and second electrodes and adjusting the output voltage V2 in response thereto so that the voltage Vs across the series pass regulator is substantially equal to the minimum voltage required to allow the series pass regulator to control the desired drug delivery current through the at least first and second electrodes and the patient's skin.

\* \* \* \* \*